United States Patent [19]

Hacskaylo

[11] Patent Number: 4,500,784
[45] Date of Patent: Feb. 19, 1985

[54] AUTOMATIC HUMAN BODY DETECTOR

[76] Inventor: Michael Hacskaylo, 3327 Prince Charles Ct., Falls Church, Va. 22044

[21] Appl. No.: 428,072

[22] Filed: Sep. 29, 1982

[51] Int. Cl.³ .................................. G01J 5/00
[52] U.S. Cl. ..................................... 250/341
[58] Field of Search ............ 250/341, 339, 342, 358.1, 250/340; 356/402 (U.S. only), 407 (U.S. only)

[56] References Cited

U.S. PATENT DOCUMENTS

| | | | |
|---|---|---|---|
| 3,210,552 | 10/1965 | Young | 356/407 X |
| 4,170,987 | 10/1979 | Anselmo et al. | 128/665 |
| 4,203,671 | 5/1980 | Takahashi et al. | 356/402 |

Primary Examiner—Janice A. Howell
Assistant Examiner—Constantine Hannaher

[57] ABSTRACT

A method is devised for the automatic detection of a human body. The method utilizes the near-infrared reflection bands of the skin of the human body as the identifying signature. Illumination of the body is provided by a near-infrared light source and the detection of the reflection bands, three in number, is performed by three detectors, each optically tuned to one of the reflection bands. When each of the three detectors simultaneously register a signal of the proper reflection values, a coincident trigger circuit enables an indicator device which signifies a human body is detected.

4 Claims, 1 Drawing Figure

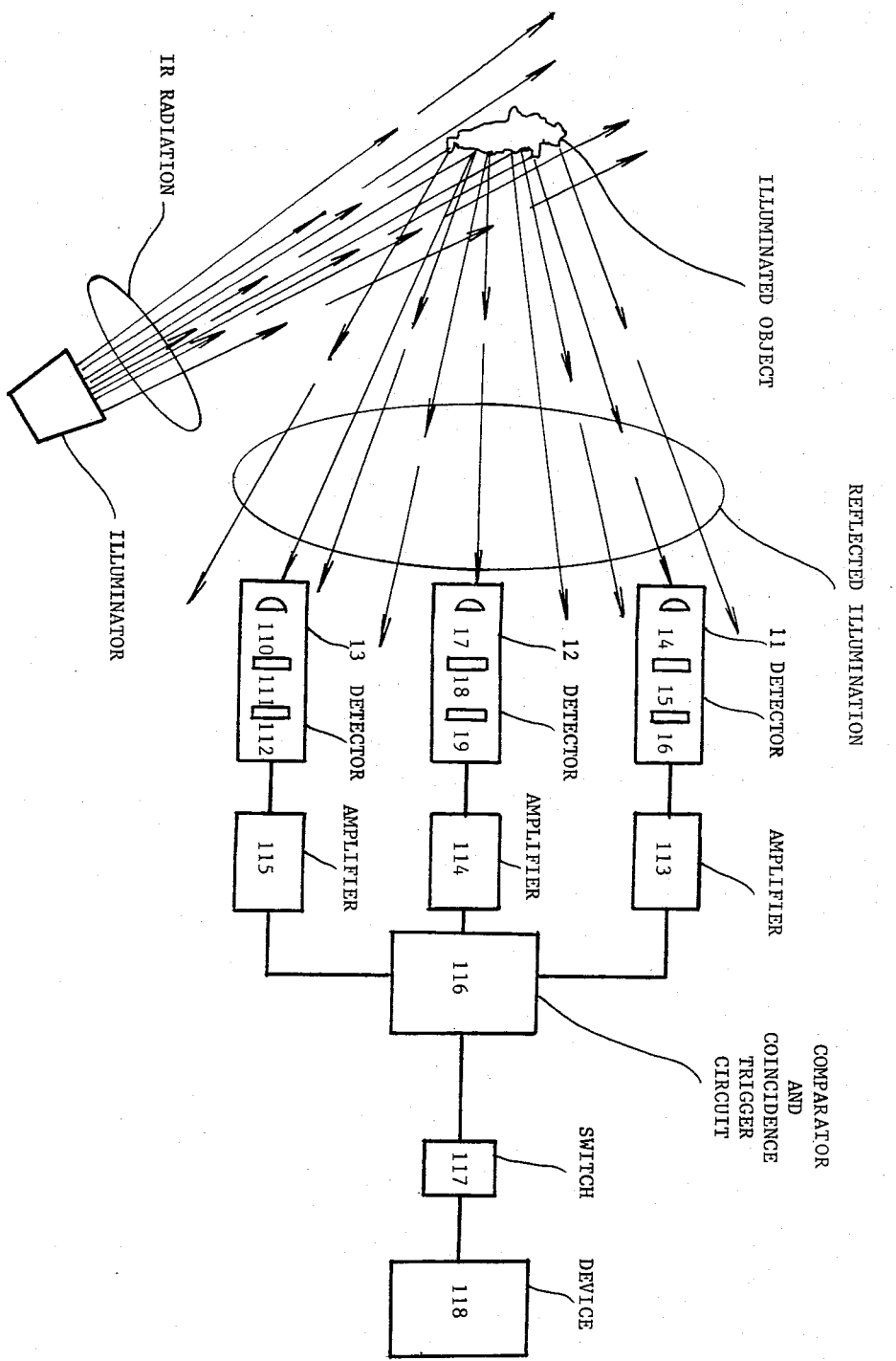

AUTOMATIC HUMAN BODY DETECTOR

BACKGROUND OF THE INVENTION

This invention relates generally to the detection of the human body by the reflection of near-infrared bands when the body is exposed to near-infrared illuminator, and more specifically to an automatic detection method of a human body under conditions which the body is not discernable by the unaided eye. Typical environments in which the detecting methods and devices are envisioned lie in the specific areas of persons lost at sea, in the forest, the desert, or in the artic regions where visual search aids do not readily acquire the identity and position of such persons. Other environments envisioned are those areas to be secured from intruders.

In a situation where a human body is in a night-time or darkened environment or in a concealed surrounds but a portion or segment of the skin is not obscured, methods for uniquely locating a human body has not been fully sucessful. Methods such as thermal viewers where the body heat radiation is detected, the position of the body becomes known but identification of the body with respect to similar heat radiating sources is unique. A recognition pattern signiture is required to identify the body, i.e., face, hands, torso, etc. for unique determination of the heat source as human. If the body should be deceased but not decomposed, the thermal viewer does not "see" the body since the thermal emission characteristics of the body would become in thermal equilibrium with the surrounds. In such cases the thermal viewer is not readily effective. The present method employs a near-infrared illumination-reflection technique which uniquely detects and identifies an object as a human body or portion of the body surface (skin) when such an object is unobscured to the illuminator-detector device.

SUMMARY OF THE INVENTION

The instant invention provides a technique for automatically detecting a human body when a portion of the body (skin) is exposed to an illuminator-detector device which detects and discriminates the near-infrared reflection bands of the skin.

BRIEF DESCRIPTION OF THE DRAWING

The single FIGURE shows a block diagram of an automatic human body detector responding to reflected illumination of an object such as a human body being illuminated with infrared radiation.

DESCRIPTION OF THE PREFERRED EMBODIMENTS

A description of the preferred embodiments of this invention may best be understood by a description of the reflection characteristics of the human body (skin) and a near-infrared illuminator as well as reference to the FIGURE, Table I, and Table II.

The human body (skin) has physical and chemical properties that reflect near-infrared light at three specific wavelengths. The reflection bands vary to a slight extent depending upon the pigment concentration and chemistry of the three major races of human species such as the dark (Negroid), medium (Oriental), and light (Caucasian) pigmentation. The reflection bands, denoted as 1,2, and 3 respectively, and the reflection in percentage for the three bands are identified and shown in Table I.

TABLE I

| BAND PIGMENTATION | 1 | 2 | 3 | 1 | 2 | 3 |
|---|---|---|---|---|---|---|
| | WAVELENGTH (MICRON) | | | REFLECTION (PERCENTAGE) | | |
| Dark | 1.27 | 1.55 | 1.78 | 48 | 33 | 14 |
| Medium | 1.11 | 1.44 | 1.67 | 48 | 36 | 13 |
| Light | 1.33 | 1.51 | 1.73 | 64 | 40 | 10 |
| (Average) | 1.22 ± 0.11 | 1.50 ± 0.06 | 1.72 ± 0.06 | 56 ± 6 | 36 ± 4 | 12 ± 2 |

The illuminator can be described without a specific drawing since an illuminator can be understood as an incandescent light of sufficient operating temperature such that a substantial amount of energy in the near-infrared region of 1 to 2 microns is emitted. The physical construction of the illuminator can be similar a flashlight or hand-held searchlight with an optical bandpass filter transmitting near-infrared light from 1 to 2 microns hereby blocking off unusable radiation wavelength.

When a near-infrared light source illuminates a portion of the exposed skin of a human body, the three bands will be reflected according to Table I. The reflected light can be detected detected with solid state detectors in the 1–2 micron wavelength range as shown in Table II.

TABLE II

| DETECTOR MATERIAL | WAVELENGTH RESPONSE (microns) | RESPONSIVITY (volts per watt) | RESPONSE TIME (microsec) | OPERATIONAL TEMPERATURE (°C.) | AREA (mm) | D* |
|---|---|---|---|---|---|---|
| PbSe | 1–4.5 | $3 \cdot 10^3$ | 1–25 | 300 | 1–10 | $10^9$ |
| PbS | 0.5–2.8 | $10^4$–$10^6$ | 100–1000 | 295 | 0.25–10 | $10^{11}$ |
| Ge | 0.5–1.8 | 0.7 | 0.005 | 300 | 1 | $10^{11}$ |

(D* is defined as centimeter root-hertz per watt)

The three reflected bands in the near-infrared region of the human body are detected and processed for signature identification as shown in the FIGURE. The reflected light from a human body is incident upon each of the detectors shown as 11 for reflection band 1, 12 for reflection band 2, and 13 for reflection band 3. Detector 11 comprises a focusing lens 14, a narrow band pass filter 15 of 1.22±0.11 microns and a near-infrared detector 16. Detector 12 comprises a focusing lens 17, a narrow band pass filter 18 of 1.50±0.06 microns, and a near-infrared detector 19. Detector 13 comprises a focusing lens 110, a narrow band pass filter 111 of 1.72±0.06 microns, and a near-infrared detector 112. The three detectors are physically arranged in a collinear manner in close proximity to each other in a common housing. The signals generated by each detector are amplified by a signal voltage amplifier 113, 114, and 115, respectively. Each amplified signal feeds into a signal comparator and coincidence trigger circuit 116 which compares the reflection voltage signals of the reflection bands 1, 2, and 3 to the normalized reflection values of 1.00±0.11 for band 1, 0.64±0.07 for band 2, and 0.21±0.04 for band 3, and at which time when the conditions are simultaneously met, the coincident trigger circuit activates a switch 117 which enables a warning device, line-of-sight orientated camera, or other appropriate device 118.

The instant invention can be readily designed and fabricated with present state-of-the-art electronics, optical, and electrooptical devices and be operational with minimal training and skills.

I claim:

1. A method of identifying an object as that of a human body by illuminating the object with infrared radiation and detecting specific bands of reflected radiation from said object, whereby the simultaneous coincidence of specific bands of reflected radiation defines the signature of the detected object as that of a human body.

2. The method of claim 1, wherein three specific reflection bands are utilized to identify the signature of a human body.

3. The method of claim 2, wherein the radiation wavelengths lying within each of said reflection bands is detected independently by detecting means responsive only to the specific bands of radiation selected but whereby the simultaneous detection of all three specific bands of radiation clearly identifies the object as a human body.

4. The method of claim 3, where the reflection bands of interest are 1.11 to 1.33 microns, 1.44 to 1.56 microns, and 1.66 to 1.78 microns, respectively.

* * * * *